United States Patent
Schlüter et al.

(10) Patent No.: US 10,282,823 B2
(45) Date of Patent: May 7, 2019

(54) SIMULATING DOSE INCREASE BY NOISE MODEL BASED MULTI SCALE NOISE REDUCTION

(71) Applicant: KONINKLIJKE PHILIPS N.V., Eindhoven (NL)

(72) Inventors: Mathias Schlüter, Ahrensburg (DE); Hanns-Ingo Maack, Norderstedt (DE); Bernd Lundt, Flintbek (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 5 days.

(21) Appl. No.: 15/528,432

(22) PCT Filed: Nov. 19, 2015

(86) PCT No.: PCT/EP2015/077155
§ 371 (c)(1),
(2) Date: May 19, 2017

(87) PCT Pub. No.: WO2016/083248
PCT Pub. Date: Jun. 2, 2016

(65) Prior Publication Data
US 2017/0345132 A1    Nov. 30, 2017

(30) Foreign Application Priority Data
Nov. 24, 2014    (EP) .................................. 14194495

(51) Int. Cl.
*A61B 6/00*    (2006.01)
*G06T 5/00*    (2006.01)
*G06T 5/10*    (2006.01)
*G06T 5/50*    (2006.01)
(Continued)

(52) U.S. Cl.
CPC ............ *G06T 5/002* (2013.01); *A61B 6/5258* (2013.01); *G06T 5/10* (2013.01); *G06T 5/50* (2013.01); *G06T 7/40* (2013.01); *G06T 11/003* (2013.01); *G06T 2207/10081* (2013.01); *G06T 2207/20016* (2013.01); *G06T 2207/20021* (2013.01); *G06T 2207/20048* (2013.01)

(58) Field of Classification Search
None
See application file for complete search history.

(56) References Cited

U.S. PATENT DOCUMENTS 5,978,518 A * 11/1999 Oliyide .................. G06T 5/007
                                                    382/260
6,252,931 B1    6/2001 Aach
(Continued)

FOREIGN PATENT DOCUMENTS

EP    0527525 A2    2/1993
EP    1345171 A1    9/2003
(Continued)

*Primary Examiner* — Kim Y Vu
*Assistant Examiner* — Nathan J Bloom
(74) *Attorney, Agent, or Firm* — Larry Liberchuk

(57) ABSTRACT

An image processing method and related apparatus. An image is decomposed into spatial frequency components images. The spatial frequency component images are normalized relative to specific noise models, remapped by a noise reduction function and are then combined to obtain a noise reduced version of the image.

11 Claims, 9 Drawing Sheets

(51) Int. Cl.
*G06T 7/40* (2017.01)
*G06T 11/00* (2006.01)

(56) References Cited

U.S. PATENT DOCUMENTS

| | | | |
|---|---|---|---|
| 2002/0071600 A1* | 6/2002 | Yamada | G06T 5/004 382/132 |
| 2004/0258325 A1 | 12/2004 | Sasada | |
| 2013/0322779 A1 | 12/2013 | Noda | |

FOREIGN PATENT DOCUMENTS

| | | |
|---|---|---|
| WO | 199701153 A1 | 1/1997 |
| WO | 2009013696 A2 | 1/2009 |

\* cited by examiner

SIMULATING DOSE INCREASE BY NOISE MODEL BASED MULTI SCALE NOISE REDUCTION

CROSS-REFERENCE TO PRIOR APPLICATIONS

This application is the U.S. National Phase application under 35 U.S.C. § 371 of International Application No. PCT/EP2015/077155, filed on Nov. 19, 2015, which claims the benefit of European Patent Application No. 14194495.9, filed on Nov. 24, 2014. These applications are hereby incorporated by reference herein.

FIELD OF THE INVENTION

The invention relates to an image processing method, to an image processing apparatus, to computer program element and to a computer readable medium.

BACKGROUND OF THE INVENTION

In digital image processing, several noise reduction methods have been developed in the past in order to improve image quality or the detectability in an image of certain structures of interest. Since in 2-dimensional images noise amplitudes increase with spatial frequency, a rather simple way of noise reduction is the application of a low pass filter which leads to a smoothing of the image. However, this method has the disadvantage, that fine structures are blurred. Another type of filters called nonlinear rank filters significantly reduce blurring effects while effectively reducing salt and pepper noise. However, for Gaussian distributed noise this kind of filtering produces undesired artifacts which are not normally acceptable for diagnostic purposes in medical imaging or in other fields of endeavor that rely on image based information gathering. Also, it is sometimes not in intuitive for a user to understand how a given noise reduction scheme works on an image.

SUMMARY OF THE INVENTION

There may therefore be a need in the art for an alternative noise reduction scheme to address at least some of the deficiencies noted above.

The object of the present invention is solved by the subject matter of the independent claims where further embodiments are incorporated in the dependent claims. It should be noted that the following described aspect of the invention equally apply to the image processing apparatus, to the computer program element and to the computer readable medium.

According to a first aspect of the invention there is provided an image processing method comprising the steps of:

receiving an X-ray image image;

decomposing said image into spatial frequency component images comprising at least a low pass component image and at least one further spatial frequency component image;

normalizing the at least one further spatial frequency component image relative to expected noise based on a noise model to obtain at least one normalized spatial frequency component image;

combining said low pass component image and the at least one normalized spatial frequency component image into a reconstructed version of the received image;

outputting said reconstructed version of the received image, wherein the combining step comprises modifying or preserving image signals of the at least one normalized spatial frequency component image in dependence on a strength of the respective image signals.

The spatial frequency component images include the high pass and the at least one further frequency component image. The at least one further frequency component image comprises at least one low pass image and, optionally, one or more band-pass images. According to one embodiment, the decomposition is effected by a recursive filter scheme where a hierarchy of band and low pass images is obtained.

The normalization step as proposed herein allows quantifying a contribution of structure versus noise for each frequency component image signal in the recorded image. This in turn allows for each frequency component image targeted damping of signals that relate to noise and/or preservation or even amplification of signals that relate to structure. More particularly, and according to one embodiment, the combining step comprises: for an image signal in at least one of the normalized spatial frequency component images, modifying or preserving said signal in dependence on whether a strength or magnitude of the image signal is inside or outside a pre-defined interval in a range of image signals. The "predefined interval" may include the case of a degenerated interval such as a threshold defined by a single number rather than a set of numbers.

According to one embodiment, the modifying comprises one of damping or amplifying.

According to one embodiment, the modifying or the preserving of the image signal is achieved by applying a function to said image signal, said function being defined on the range of image signals.

According to one embodiment, said function is monotonically increasing over said range of image signals.

According to one embodiment, said function is continuously differentiable. In other words, in this embodiment, the function smoothly transitions from a region where the function acts as damper to one where it acts as a preserver or amplifier.

According to one embodiment, the strength of the image signal damping or amplifying is adjustable or variable. In particular, the said strength may be user adjustable.

According to one embodiment, the noise model is different for different ones of the spatial frequency component images. In other words, the noise model is band-pass or high-pass specific.

According to one embodiment, the strength of the damping relates to a virtual X-ray dose increase. This allows "simulating" a noise reduction that could have been achieved had the image been acquired with a higher dose.

According to a second aspect of the invention there is provided an image processing apparatus, comprising:

an input port configured to receive an image;

a decomposer configured to decompose said image into spatial frequency component images comprising at least a low pass component image and at least one further spatial frequency component image;

a normalizer configured to normalize the at least one further spatial frequency component image, relative to expected noise based on a noise model, to obtain at least one normalized spatial frequency component image;

a combiner configured to combine said low pass component image and the at least one said normalized spatial frequency component image into a reconstructed version of the received image;

an output port configured to output said reconstructed version of the received image, wherein the combiner comprises a selective modifier configured to modify or preserve image signals in the at least one normalized spatial frequency component image, the modifying or preserving being in dependence on a strength of the respective image signals.

More particularly and according to one embodiment, the combiner comprises a selective modifier configured to modify or preserve an image signal in at least one of the normalized spatial frequency component images, the modifying or preserving being in dependence on whether the strength of the image signal is inside or outside a pre-defined interval in a range of image signals.

According to one embodiment, the modifying of the selective modifier is one of damping or amplifying.

According to one embodiment, the modifying or the preserving of the image signal by the selective modifier is achieved by the selective modifier applying a function to said image signal, said function being defined on the range of image signals. According to one embodiment, said function is monotonically increasing over said range of image signals.

According to one embodiment, said function is continuously differentiable.

According to one embodiment, a strength of the image signal damping or amplifying is adjustable.

According to one embodiment, the image received at the input port is an X-ray image and wherein the strength of the damping relates to a virtual X-ray dose increase.

According to one embodiment, the noise model used by the normalizer is different for different ones of the spatial frequency component images.

It is an objective in medical x-ray imaging to reduce to a minimum of dose applied to a patient, preferably without loss of diagnostic quality. On the other hand dose increase has been recognized as one way of noise reduction of whilst preserving contrasts. In this sense a dose increase may be regarded as a "gold standard" for a noise reduction algorithm. The present method and apparatus harnesses this observation to arrive at a noise reduction algorithm guided by the principle of how to simulate in a computationally efficient way a dose increase. In other words, the noise reduction algorithm as proposed herein has, at least for acquired anatomical structures with strong contrasts, a similar noise reducing effect as an X-ray dose increase would. In one embodiment, the proposed apparatus features an intuitive user interaction functionality that allows the user to control the amount of noise reduction by a parameter which is related to a physical modeling of an increase in X-ray dose. To achieve this simulated effect of dose increase, image signal noise is modeled as a function of x-ray dose. This kind of modeling leads to a physical noise model which is specific for a particular x-ray detector used to acquire the received image to which the proposed noise reduction method or apparatus is to be applied. In this sense, the current method and apparatus describe the simulation of dose increase by noise model based noise reduction.

In sum, what is proposed herein in one embodiment is a noise reduction method and apparatus that simulates the effects of dose increase on noise. Herein the desirable level of dose increase is in one embodiment an adjustable parameter of the method and apparatus. For this purpose the noise is modelled as a function of X-ray dose. Such noise model is detector specific. Noise reduction is performed on the decomposition of the X-ray image into multiple frequency bands. Each such frequency band is normalized in terms of noise based on frequency band specific modelled noise. The effect is a noise reduction as would be obtained by a dose increase.

It should be noted that "normalizing" the spatial frequency image (such as the high or band-pass image) may not necessarily imply that each and every pixel is normalized although in most use scenarios the operation will be exhaustive. There may however be certain use scenarios where it suffices to normalize merely a true sub-set of the image signals recorded in some or all images. Similarly for the "modification" or preservation operation when combining/reconstructing the (at least partly) normalized images. Here too, it may be occasionally sufficient to consider merely a true sub-set of the image signals recorded in some or all (at least partly) normalized images. Also, the normalized/modified/preserve may be applied to different extents in different levels of the hierarchy levels in the decomposition. For instance, in one level all image signals are normalized or considered for modification or preservation whereas in other levels only a true subset of image signals is normalized and/or considered for modification or preservation.

BRIEF DESCRIPTION OF THE DRAWINGS

Exemplary embodiments of the invention will now be described with reference to the following drawings wherein.

DETAILED DESCRIPTION OF EMBODIMENT

Figure 1:
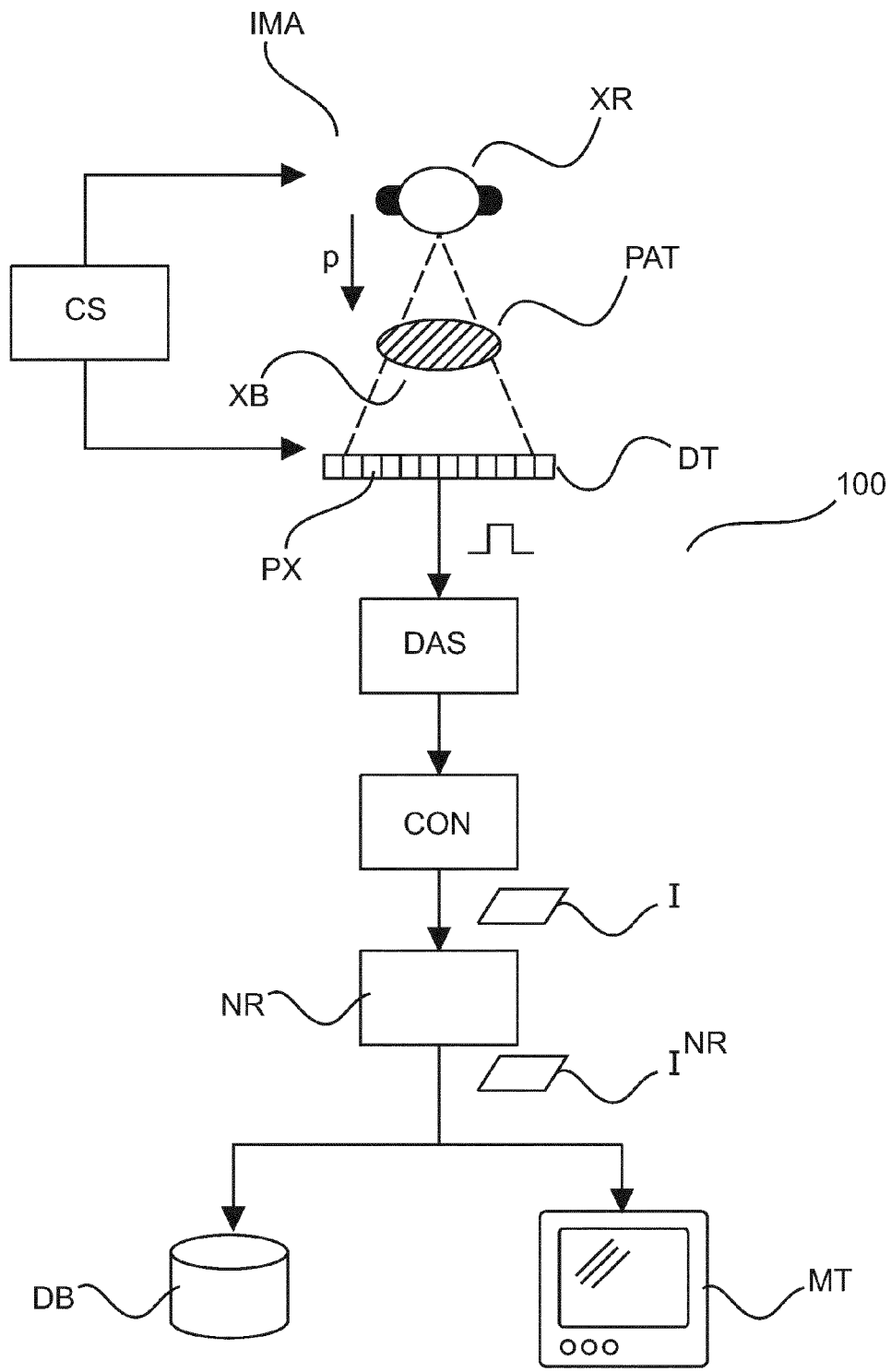
FIG. 1 shows an imaging arrangement.

With reference to FIG. 1 there is shown an imaging arrangement 100 comprising an x-ray imaging apparatus IMA. The imaging apparatus IMA includes an x-ray source (an x-ray tube) XR and an x-ray sensitive detector DT. Preferably, but not necessarily, the detector is of the digital flat panel type. The x-ray source XR and the detector DT are supported in a gantry (not shown). The x-ray imaging apparatus IMA may be one of CT scanner or planar imager such as a C-arm or U-arm x-ray imaging system as used in interventions or a diagnostic x-ray system. However other types of x-ray imagers are also envisaged herein. Operation of the imager IMA is controlled by a user or by an imaging protocol via an operation console CS.

The specimen under investigation for instance human or animal patient PAT is positioned on a support (not shown) between the x-ray source XR and the detector DT. For each pixel PX of the detector DT the received signal is proportional to the x-ray dose collected at this pixel. The individual analog signals are then picked up by suitable circuitry, more particularly by a data acquisition system DAS. The DAS includes in particular an analogue to digital (A/D)-conversion circuitry which converts analog signal into a digital value, that is, into a number, measured in least significant bits (lsb). These digital values are also referred to herein as "pixel values" or "image signals". The collection or array of all digital values so obtained forms an x-ray image I=(k,l), with (k,l) denoting the array index of the respective pixel position. The image I may then be forwarded to a monitor MT or may be stored in a memory such as a data base DB or may be otherwise processed.

In particular the digital values of the x-ray image are passed on to a graphical renderer which maps the digital values according to scale such as a grey value palette or color palette. The mapped values are then used to drive the monitor MT via suitable graphics software to effect the rendering on the screen MT.

In some embodiment, but not necessarily in all embodiments, the imaging arrangement 100 may include a conversion unit or mapper CON through which a domain conversion or mapping of the image signals can be achieved. In particular, since the attenuation of the x-ray beam depends exponentially on the thickness of the interacting matter, it is frequently convenient to express the registered digital values as picked up at the detector through logarithmic values. Within this logarithmic domain signal contrasts are proportional to the thickness differences and independent on the x-ray dose. In other words the converter operates to convert the digital values from the registration or linear domain into a logarithmic domain. The linear domain is formed from the signals as detected by the detector. The magnitude or "strength" of the individual image signals in this domain is proportional to the detected dose at the respective pixel associated with pixel value (k,l). The dose domain transformation is done for instance so that the contrast information from different images is comparable, for instance according to the logarithmic scale. Alternatively to this contrast stabilizing transformation a so called "variance-stabilizing transformation" can be applied. See for instance, Y Dodge in "The Oxford Dictionary of Statistical Terms", OUP (2003). After this transformation the variance of the noise is signal or dose independent. The domain mapping or conversion (and hence converter CON) is optional and the noise reduction apparatus as proposed herein may also operate directly on the digital values in the linear domain as registered at the detector-DAS stage. Because of the noise normalization the present invention can be applied to arbitrary dose domains. For a certain dose domain mapping, a noise model (as will be explained in more detail below at equations (4),(5) of the linear dose domain (see FIG. 2) is transformed accordingly. For this reason the present invention can be combined with other multi scale image processing steps as described in FIGS. 3 and 4.

The x-ray image signals are often corrupted by noise due to a number of factors which will be explained in more detail below. This makes ascertaining of delicate structures sometimes difficult if not impossible. As proposed herein, and to combat this noise, the imaging arrangement 100 includes a noise reduction module NR that operates on the detected image (or if applicable, on the converted image) to produce a noise reduced version $I^{NR}$ of the image.

Figure 3:
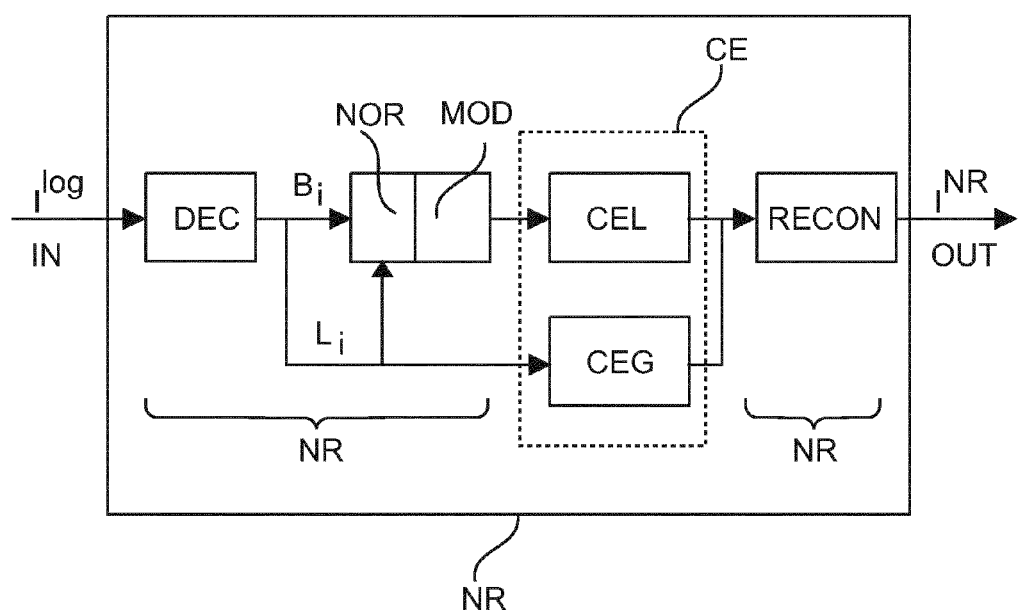
FIG. 3 shows a block diagram of a noise reduction apparatus.

With reference to FIG. 3, there is shown a block diagram showing some basic components of the noise reduction module as proposed herein. The noise reduction module NR includes one or more input ports IN and one or more output ports OUT. The noise reduction module includes an image de-composer DEC, a normalizer NOR, a signal modifier MOD and a reconstruction unit RECON to reconstruct the previously decomposed image signals. Optionally there is also a signaling enhancement unit CE.

Very broadly, the image I to be processed or noise reduced is received at input port IN. The multi-scale spatial frequency decomposition module DEC operates to decompose the image into a hierarchy ("Laplacian" pyramid) of a different band-pass images $B_i$ and corresponding low pass images $L_i$. There is also a high pass component H. The band pass components $B_i$ (and the high pass component H) are first noise normalized and then selectively modified or remapped by operation of the modifier MOD. The (pixel-wise) modification operation is selective because, depending on the configuration of the modifier MOD and the strength/magnitude of the image signal in the respective normalized band-pass (and high-pass), the image signal is either i) preserved (so is not modified) or damped or ii) preserved or amplified or iii) is preserved or damped or amplified. In each of the possible MOD configurations i)-iii), the nature of the action (preservation, damping, amplification) depends on the strength/magnitude of the image signal in the respective normalized band-pass (and high-pass) mage signal. Notably, said modification is not applied to the low pass components $L_i$ in each hierarchy but low pass components $L_i$ are used to compute the signal dependent noise information (e.g. standard deviation) to quantify local noise at the respective image signal and to use this information in the normalization operation of the band pass and/or high pass images. Optionally, the low pass components and the MOD-processed high and/band components may be passed onto a contrast enhancement stage as described for instance in DE 19 849 090.

According to one embodiment this optional contrast enhancement stage includes a local contrast enhancement component CEL and a global enhancement component CEG. The local contrast enhancement component CEL operates on the high pass and/or band pass components whereas the global enhancement component CEG operates on the low pass components. The so noise reduced components after optional contrast enhancement are then passed on to the re-constructor that operates to iteratively reconstruct the so modified frequency components to produce at output stage OUT the noise reduced version of the received image.

Figure 4:
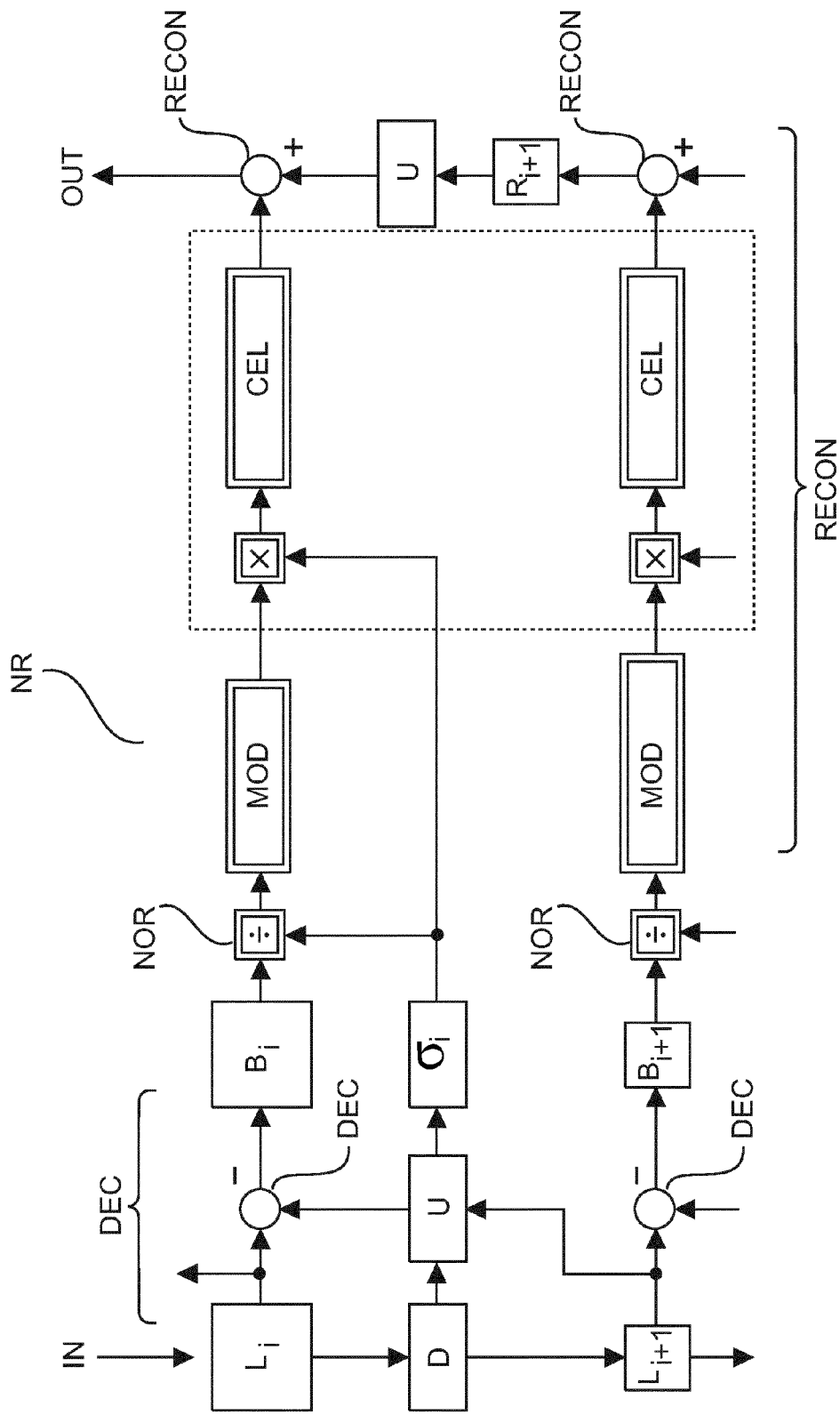
FIG. 4 shows a more detailed block diagram of various stages of the noise reduction apparatus of FIG. 3.

Reference is now made to FIG. 4 to illustrate more details of the operation of the noise reduction module of FIG. 3 for a given level i in the Laplacian decomposition pyramid. Operation in said exemplary level are now explained in more detail, with the understanding that the following holds true for any level i in the Laplacian hierarchy.

The operation boxes D and U denote, respectively, a down sampling operator and an up sampling operator combined with a low pass filtering (se equations (1)-(3) below). Operation box "$\sigma_i$" indicates a respective theoretical noise model to be used in the various levels i as will be explained in more detail below with reference to FIG. 5 in particular. For a certain level i in the hierarchy, the respective higher level low pass component $L_{i+1}$ is up sampled so as to match in size the low pass image $L_i$ of the current level i. The up sampled low pass image $L_{i+1}$ is then subtracted from the low pass component Li to produce a band pass component $B_i$ for the said level i.

Individual pixels in the band pass image at the current level $B_i$ (in similar to the high pass component H) are now processed as follows: For an image signal in the considered band pass component $B_i$, a low pass signal dependent noise level is computed based on a theoretical noise signal model, exemplary designated in the block diagram as "$\sigma_i$". Briefly, the $\sigma_i$ block represents the computation of the expected standard deviation $\sigma$ for the noise in the upper band pass as will be described in more detail below at FIG. 5. The noise level is computed at the corresponding position from the up sampled low pass image $L_{i+1}$ from the higher level. This can be done because, due to the up sampling, the two images have the same size so pixel position (k,l) from the band pass image $B_i$ corresponds to the same pixel (k,l) position in the up sampled low pass image $L_{i+1}$. The band pass signal at the considered pixel position (k,l) is then normalized relative to the so computed noise level which in this embodiment is measured by a standard deviation value for the noise.

Normalization can be implemented by forming pixelwise quotients that is by dividing the respective image signal at said position (k,l) in component $B_i$ by the computed standard deviation $d_i$ of the noise, to obtain for some or each pixel positon in the band pass image a respective local contrast-to-noise ratio CNR value. The same is done for the high pass image where the noise is computed from low pass image $L_0$. The respective local CNR ratios so obtained are then modified selectively by a modifier MOD. The modifier acts either to preserve (or even to amplify) the local contrast noise ratio $B_i/\sigma_i$ or to dampen this value by applying suitable weights computed, in one embodiment, from a noise reduction function $f^{NR}$. Briefly, the noise reduction function $f^{NR}$ operates as a remapper to selectively reduce noise but to preserve informational signals from a real structure as recorded in the image. Instead of merely preserving the structure representing values, in one embodiment the function may operate to amplify those structure representing signals. The so modified values are then multiplied by the computed noise contribution (for instance, the standard deviation $\sigma_i$ as per the respective noise model for the current level i) and the so re-weighted band pass signal is then forwarded to the reconstruction stage. Optionally, prior to reconstruction a contrast enhancement stage may be applied. The previously applied procedure is repeated for the band pass image in each level and for the high pass component and the respective image signals are then iteratively reconstructed (with the low pass components) at reconstruction stage to produce at the output OUT the noise reduced image $I^{NR}$.

In FIG. 4, the global contrast enhancement stage (based on a "film" density curve) is applied to the last low pass image is not shown. Furthermore, the processing of the high pass H is not shown because this is similar to the band pass processing, except that there are no down- and up-sampling operations. The reconstructed low pass in level i is denoted by $R_i$ Reference is now made to the flow chart in FIG. 5 where operation of the proposed noise module NR is explained in more detail.

At step S505 an x-ray image I is received.

At step S510 multi scale decomposition is performed on the received image to decompose the image into a plurality of frequency component images. More particularly an extended multi-scale decomposition is performed by decomposing the x-ray image I into multi scale frequency bands, where each of them corresponds to a characteristic structure size. Let D=↓ $F_m$, U=$F_m$ ↑ be down and up sampling operators, where $F_m$ denotes an m by m (typically 5-by-5 or 3-by-3 but any other size is also envisaged) binomial low pass filter and "↓" and "↑" denote elementary down and up sampling operators, respectively. To be more specific ↓ removes every second pixel and ↑ inserts zeros between any two neighboring pixels to form a "checkerboard" of zeros and the original image signal values. Now the decomposition is performed by separation of a high pass H and iterative calculation of multi scale low and band passes $L_i$ and $B_i$ as per the following recursive decomposition routine:

$L_0 = F_3 I$ $H = I - L_0$ $L_{i+1} = DL_i$ $B_i = L_i - UL_{i+1}, i=0, \ldots, n-1$  (1)

This defines a hierarchy of levels, or a "Gaussian" and a "Laplacian" pyramid with i=0 forming the highest frequency level. The index i is merely to number the frequency bands. The exact center frequency (e.g. 2 to 4 lines per millimeter or similar to name but one numerical example for the sake or definiteness) and bandwidth will depend on the particular low pass filters $F_m$ used.

A corresponding, standard recursive reconstruction of image I can then be obtained as follows:

$L_i = UL_{i+1} + B_i, i=n-1, \ldots, 0$ $I = H + L_0$  (2)

Now, with the decomposition defined above, the image I can be expressed as a sum of the high pass H, the multi scale band passes $B_i$ and the last low pass $L_n$;

$$I = H + \sum_{i=0}^{n-1} U^i B_i + U^n L_n \quad (3)$$

Figure 5:
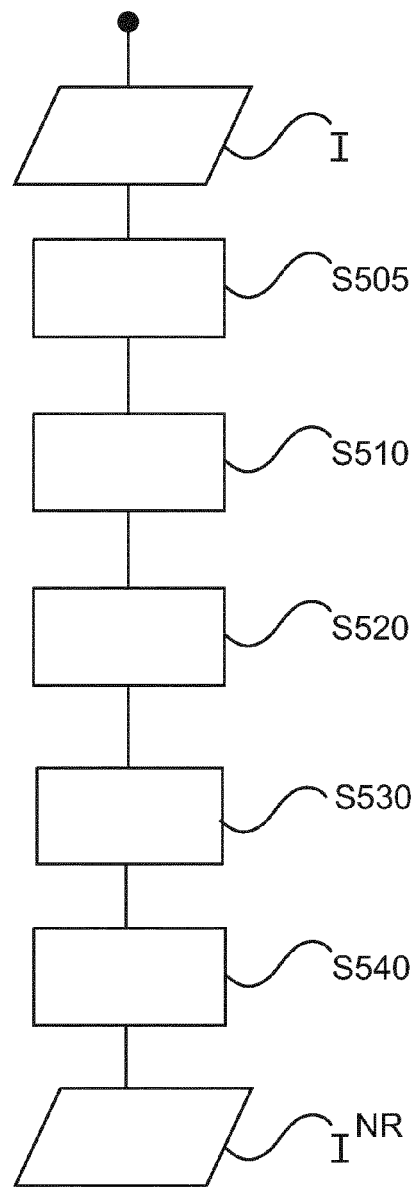
FIG. 5 shows a flow chart of an image processing method.

It is this representation of the image as a sum of frequency components (H, $B_i$ an $L_n$) that will be exploited for a noise reduction processing as will be explained in more detail with reference to FIGS. 3-5.

It will be appreciated however, that any other band pass decomposition algorithm is also envisaged herein, the above decomposition (3) being but one embodiment. What is required is that the band passes are "average free" (the operation of $F_3$ or D in (1) can be understood as an averaging and the averages are then subtracted for H and each $B_i$) and the noise in the last low pass $L_n$ in the Gaussian hierarchy 0 . . . n having a maximal standard deviation which is negligible compared to the minimal structure contrasts (e.g. a standard deviation less than 1 lsb).

At step S520 the component images are normalized relative to band specific noise model to obtain for each of the bands a normalized spatial frequency component images. The same procedure is applied to the high pass image. The normalization is not envisaged to be applied to the low pass images however. Much rather the low pass contrast images are thought to encode the noise information. The noise information is retrieved by applying a noise model function to the respective low pass images, to extract the noise information for the particular pixel of the band or high pass image. The noise model can be applied directly to image signals as detected at the detector. However, the detector signals may be first transformed into a different domain (for instance a logarithmic domain as explained earlier) and the noise model can then be transformed accordingly. In the following more details are provided as to the noise model and the band specific noise model to be used as proposed herein.

Turning now to the particulars of the noise model, the output signal of x-ray detector DT (as briefly mentioned above at FIG. 1) is proportional to the amount of photons which are Poisson distributed. For a Poisson distribution the variance is proportional to its mean value. This stochastic variation of the received photons is called quantum noise. If the amount of photons is large, the Poisson distribution can be approximates by a Gaussian distribution with a variance equal to its mean value. Thus the variance of the quantum noise contribution to the detector signal is proportional to the received dose which is again proportional to the detector signal. We denote the proportionality constant between linear detector signal and variance by the coefficient q. Another contribution to the variance of the detector signal is noise from electronic components of the detector. This noise is dose independent and we denote it by the coefficient e. Due to internal structures of the detector and inaccuracies in the gain table we have a third fixed pattern contribution to the variance of the detector signal which has a quadratic dependence on the dose. We denote the corresponding fixed pattern coefficient by f.

Thus for the linear detector signal $s^{lin}$ we obtain a $2^{nd}$ order polynomial dependency of the variance on the detected dose. The standard deviation of linear signals can then be written as:

$$\sigma^{lin}(s^{lin}) = \sqrt{e + q s^{lin} + f_s s^{lin^2}} \quad (4)$$

Figure 2:
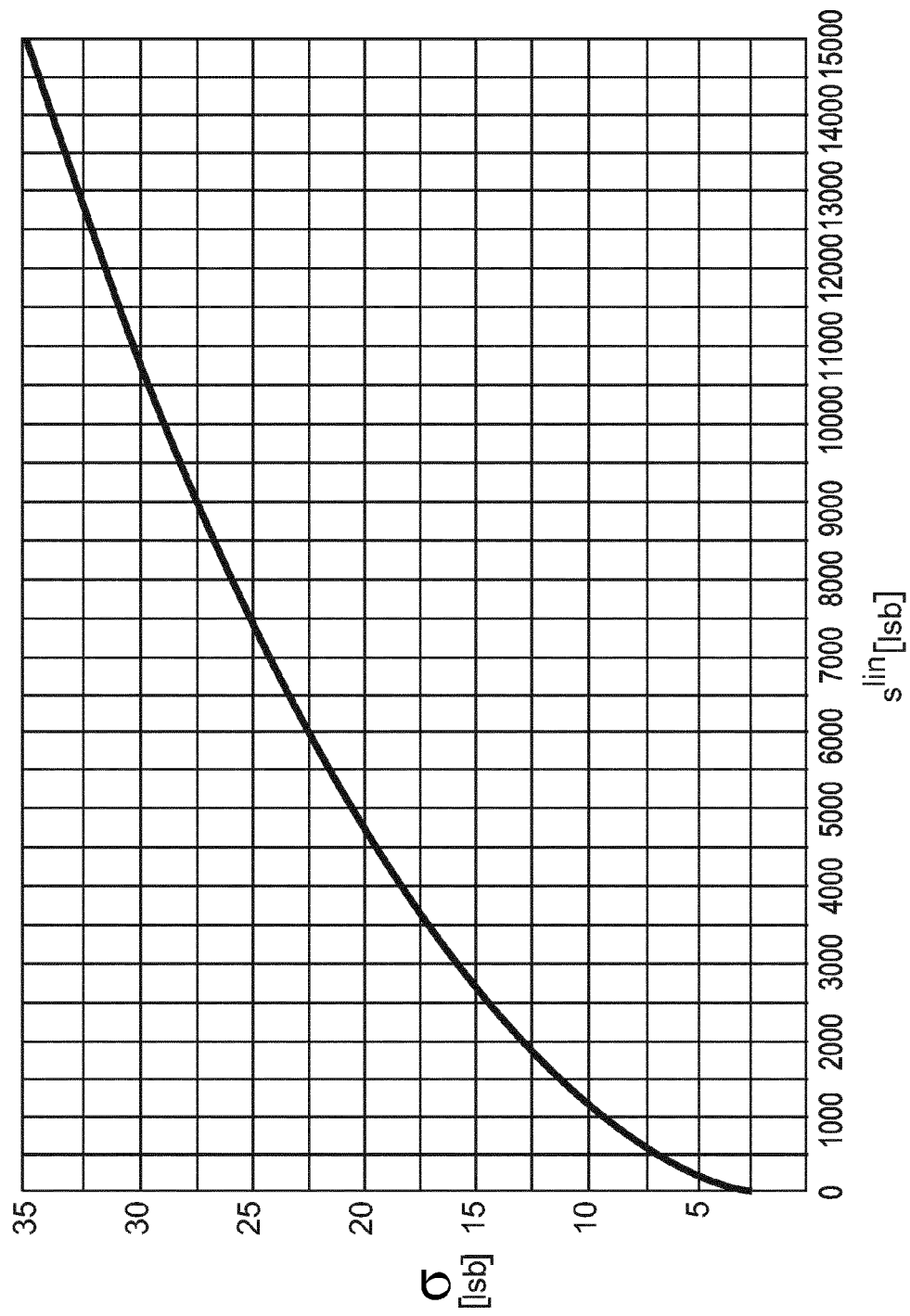
FIG. 2 shows a various noise model parameters.

This (parameterized family of) noise model(s) is illustrated in FIG. 2.

Due to the point spread function of the detector, which acts on the quantum signal, the noise model depends on the spatial frequency. This can be expressed by high and band pass specific noise coefficients:

$$\sigma_i^{lin}(s^{lin}) = \sqrt{e_i + q_i s^{lin} + f_s s^{lin^2}} \quad (5)$$

where the index i=H; 0, . . . , n−1 denotes the high pass and the band passes. In other words, it is proposed herein to use different, band/-high-pass specific noise models throughout the hierarchy i=H; 0 . . . n.

For an arbitrary dose domain mapping M on a dose domain x:

$$s^M = M(s^x) \quad (6),$$

the dose dependent noise transforms for small signals according to:

$$\sigma^M(s^M) \approx M'(s)\sigma^x(s) = M'(M^{-1}(s^M))\sigma^x(M^{-1}(s^M)) \quad (7),$$

where M' is the first derivation of the mapping M. Thus, once we have determined the noise model in the linear dose domain, we can predict the noise in any other domain. For the log dose domain we obtain:

$$s^{log} = d \log(s^{lin}) \quad (8)$$

$$\sigma^{log} = \left(\frac{d}{s^{lin} \ln 10}\right)\sqrt{e_i + q_i s^{lin} + f_i s^{lin^2}}, \quad (9)$$

where d denotes a scaling constant. The log dose noise can be expressed as a function of the log dose signal $s^{log}$, by inverting the first equation and inserting the linear signal into the second equation. It turns out that the log dose noise decreases exponentially with increasing log dose signal.

At step S530 the normalized spatial frequency component images $B_i$, H are combined with the low pass images $L_i$ to so compute the noise reduced image $I^{NR}$. The combination operation can be implemented based on the recursive reconstruction algorithm outlined above as per recursion (2), (3). As proposed herein, according to one embodiment, the reconstruction formula (3) is adapted by inclusion of an image signal dependent noise reduction function $f^{NR}$ that induces a preservation or a modification of the normalized image signal depending on the strength of that signal. More particularly, a multi scale noise reduction is proposed herein that is defined on the decomposition representation of the original image I:

$$I^{NR} = f^{NR}(H/\sigma_H)\sigma_H + \sum_{i=0}^{n-1} U^i f^{NR}(B_i/\sigma_i)\sigma_i + U^n L_n \quad (10)$$

where the noise reduction function $f^{NR}$ is some monotonic increasing function. This formulation is independent of the dose domain. For a multi scale level i, the noise $\sigma_i$ is computed by applying the noise model for the current dose domain to the up scaled low pass of the successive level:

$$\sigma_i = \sigma_i(UL_{i+1}) \quad (11)$$

In other words, for each level i and band pass $B_i$ (or for the high pass image H), the required noise information for the normalization is obtained by fetching the image signal from an up-sampled low-pass image from a different level (for instance from a higher level such as the low-pass $UL_{i+1}$) at the respective pixel position. Here we take advantage of the fact that the noise depends on the original image signal which is present in $UL_{i+1}$ as a smoothed version.

Note that the noise reduction function $f^{NR}$ is applied to the noise normalized high and band passes, which can be regarded as band specific CNRs as mentioned above. For these band specific CNRs, the standard deviation of noise within homogeneous regions is dose independent and equal to one. At object borders the band specific CNRs increase with the square root of the received dose. An illustration of an effect of the multi scale noise reduction is illustrated below in FIG. 8 by way of exemplary imagery.

The noise normalized high and band pass signals ($H/\sigma_i$ and $B_i/\sigma_i$, respectively) are symmetrically distributed around zero and objects have statistically a higher signal than noise. This implies the following requirements on the noise reduction function $\sigma^{NR}$:

point symmetry around zero
monotonically increasing
damping (or suppression) of "small signals"
preservation or even amplification of large signals Some properties of the noise reduction function are summarized in Table 1 The following function fulfills these requirements and furnishes an exemplary embodiment for the noise reduction function $f^{NR}$:

$$f^{NR}(y) = y\left[(a_{max} - a_{min})\frac{\tanh\left(\left(\frac{\gamma}{2(a_{max} - a_{min})}\right)\left(\frac{y^2}{y_0^2} - 1\right)\right) + t_0}{1 + t_0} + a_{min}\right] \quad (12)$$

with $$t_0 = \tanh\left(\frac{\gamma}{2(a_{max} - a_{min})}\right),$$

where y is the noise normalized band signal.

With this function as per (12), which is merely according to one embodiment, a smooth transition between noise reduction and preservation/amplification of structures can be modeled. More particularly, the location of inflection point $y_0$ controls the location of where (that is, at which image signal magnitude or over which interval) the transition occurs and $\gamma$ controls the strength of the transition, that is, how smooth this transition is.

Figure 6:
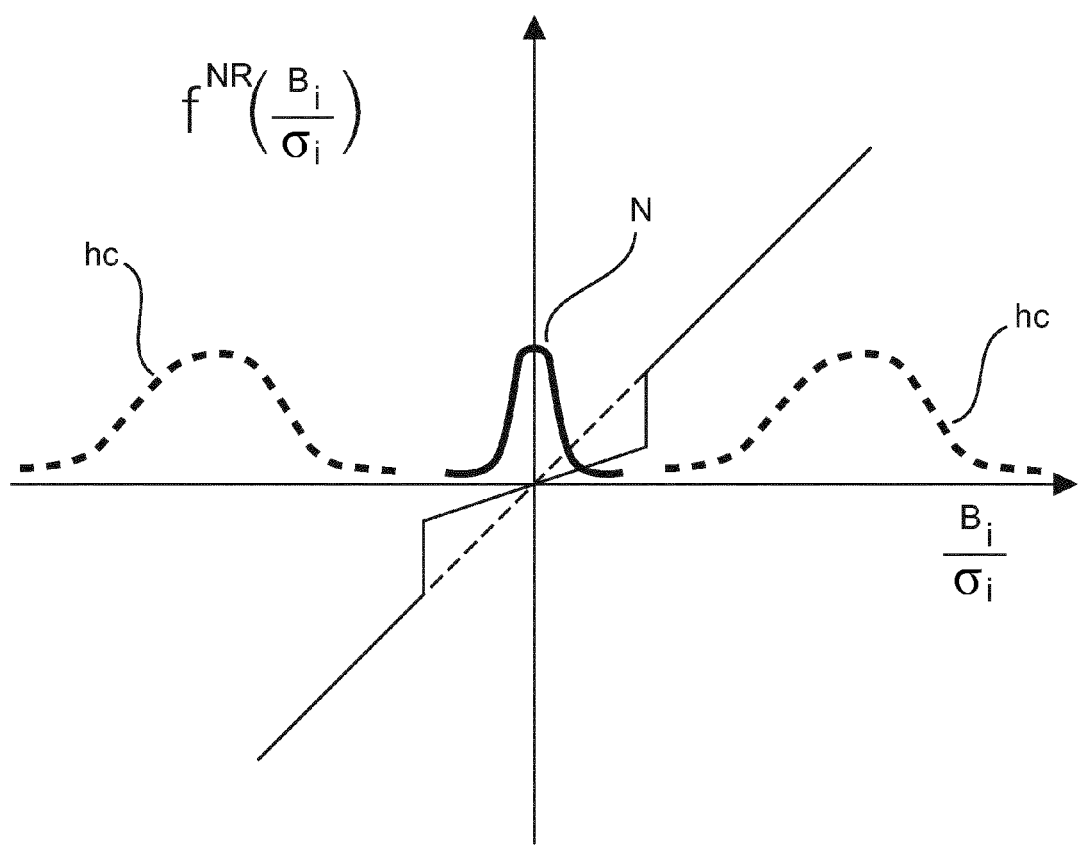
FIG. 6 shows an idealized version of a noise reduction function.
Figure 7:
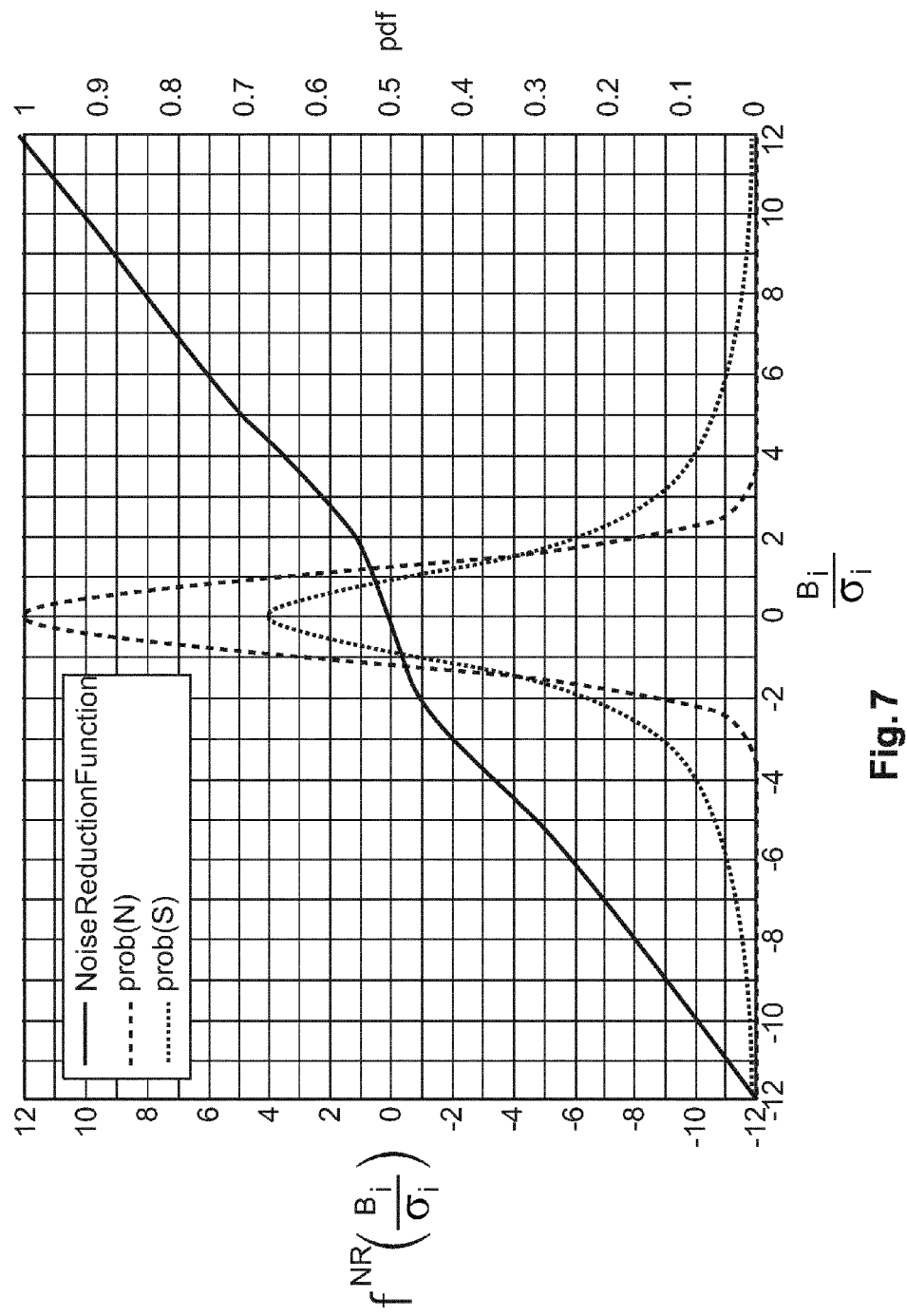
FIG. 7 shows another version of a noise reduction function.

Table 1 summarizes some properties of the noise reduction function and FIGS. 6,7 illustrate the noise reduction function graphically:

TABLE 1 summary of noise function properties

| Property | Description | Remark |
|---|---|---|
| $f^{NR}(-y) = -f^{NR}(y)$ | point symmetry around zero | symmetric noise reduction for positive and negative band signals |
| $f^{NR'}(y) \geq f^{NR'}(0) = a_{min} > 0$ | strictly increasing noise reduction function, maximum damping at zero | the order of band signals is not changed, adjustable damping of small signal |
| $f^{NR}(y) = a_{min} y$ for y in interval $\|y\| \ll y_0$ ($y < y_0 + \varepsilon$) $[-\varepsilon, \varepsilon]$ | damping of small signals | $0 < a_{min} < 1$ |
| $f^{NR}(y) = a_{max} y$ for $\|y\|$ in interval $[\theta, \infty]$ with $\|\theta\| \gg y_0$ | preservation ($a_{max} = 1$) or amplification ($a_{max} > 1$) of large signals | $a_{max} \geq 1$ |
| $a_{min} y_0 < f^{NR}(y_0) < a_{max} y_0$ $f^{NR'}(y_0) = (a_{min} + a_{max} + \gamma)/2$, for $\|\gamma\| \gg 1$ | smooth transition from damping to preservation with increasing signal amplitude | The location of inflection point is controlled by $y_0$. It is some multiple of the expected noise amplitude. The transition from damping to amplification/preservation is controlled by the slope $\gamma$. In the limit $\gamma$ to infinity $f^{NR}$ degenerates to a step function as shown in FIG. 6 |

Not each embodiment of a noise reduction function $f^{NR}$ may necessarily fulfill all these properties however and it may be sufficient in some embodiment for the function to fulfill merely one or some of said properties. The requirement for monotonicity however is necessary in all embodiments.

As can be understood from the properties of function $f^{NR}$ above, the present reconstruction or combination step includes either modifying (that is damping or amplifying) or preserving of the image signals in the normalized band pass or high pass image. Whether a modification or preservation is applied depends on magnitude of the image signal and the chosen configuration i)-iii) (as explained above at FIG. 3) of modifier MOD in particular the chosen configuration of the noise reduction function. For instance, $\alpha_{min} < 1$ effects a damping of small signals and $\alpha_{max} = 1$ or $a_{max} > 1$ effects a preservation or an amplification action. This is explained in more detail below at FIGS. 6,7.

The modification or preservation operation is applied/decided pixelwise in the respective normalized band pass or high pass image. To better understand the transformation (that is modifying or preserving) of the normalized band pass or high pass image by operation of noise reduction function $f^{NR}$ it will be convenient to recall what the pixels in each of these normalized images ($H/\sigma_i$ or $B/\sigma_j$) actually encode. Each image signal as recorded at the detector can be understood to comprise of an actual signal that stems from a structural feature and a noise signal component. The pixel values in the normalized band pass or high pass signal then represent the amount by which either one of the two components dominate. For instance, a pixel value of around zero in the normalized band pass or high pass image means that one can expect, statistically, a preponderance of noise as compared to a structural signal. On the other hand, a negative or positive signal away from zero represents a tendency for a preponderance of the actual structural signal as compared to the noise component. In other words the normalization step at S520 as proposed herein allows us to quantify in a rational manner the preponderance of noise versus structure at the respective pixel position and to then selectively either to suppress or to preserve or even to amplify the respective image signal. It is proposed herein to define certain action intervals around zero (which may be specific for each pixel and/or each band/high pass). If the image signal in the normalized band pass or high pass is within said interval, then damping is applied to these values. The amount of damping can be either controlled by the user or pre-programmed by the designer. If however the image signal in the normalized band/high pass is outside said interval, the signal is expected to represent rather structure than noise and the normalized band or high pass image signal is therefore either amplified or at least preserved. Whether the modifying operation is one of amplification or preservation is user adjustable according to one embodiment or is pre-programmed by the designer.

Whether the action is one of preservation or modification is defined in one embodiment by the functional properties or "shape" of the noise reduction function $f^{NR}$ as given in Table 1. In an alternative embodiment, a look-up table may be provided which lists a damping or a modification action versus certain intervals of image signal values. The noise reduction module may then include a decision logic which determines in which interval the respective image signal value at a certain pixel falls. It then looks up the associated action and applies for instance a weighing factor to either suppress or to amplify (or at least preserve) the respective pixel value. In other words the noise reduction function may not necessarily exist in a closed form as in the embodiment (12) above. Also, the function $f^{NR}$ may be defined in a piece wise fashion and certain numerical techniques such as splining may be applied to achieve the smooth transition zones between the damping region and preservation or amplifying region.

To better understand the significance of the nose reduction parameters $\alpha_{min}$, $A_{max}$, $y_0$ and $\gamma$ it is instructive to now refer to FIG. 6 where an idealized version of the noise reduction function $f^{NR}$ is graphed. The horizontal axis represents the normalized signals Bi divided by $\sigma_i$ whereas the vertical axis represents the respective value after application of the noise reduction function $f^{NR}$ (Bi/$\sigma_i$). FIG. 6 shows an idealized scenario. In other words, at around zero there is only noise and no structural signal whereas away from zero there is only structural signals (high contrast) and no noise. The probability densities for structural signals are indicated as $h_C$ whereas the probability density for noise is indicated by N. In such an idealized scenario the noise reduction function $f^{NR}$ may look like the identity function with a "kink" at the origin. In other words, the graph of $f^{NR}$ has a slope less than unity in the damping interval and equals unity (or is larger than unity) outside this interval. In other words, the high contrast signals are preserved whereas signals within the damping or suppression zone are suppressed by application of damping factor $\alpha_{min} \leq 1$. The strength of the damping action can be adjusted by choosing $\alpha_{min}$ accordingly: the smaller $\alpha_{max}$, the larger the damping action. Also, as a variant of the above, rather than merely preserving the high contrast values the normalized values y may be amplified by applying a factor $\alpha_{max}$ larger than unity. In other words, the preservation or amplification is always applied to image signals where there is a preponderance (or a higher probability) of a structural signal. Any other signal is thought to include more noise and is therefore "punished" by application of the suppression or damping factor $\alpha_{min} < 1$. In reality however, there is rarely such artificial separation between noise and structural signal as shown in FIG. 6 (although in some real world scenarios the kinked step function of FIG. 6 may be sufficient and its use is envisaged herein in some embodiments).

FIG. 7 shows an alternative embodiment of the noise reduction function $f^{NR}$ as defined in equation 12 which may be understood as a "smoothed" version of the FIG. 6 embodiment to account for the fact that in reality an image signal is usually a combination of both. The axis labelling in FIG. 7 is similar to the one in FIG. 6. The two bell shaped curves show the respective probability density functions of structure and noise versus the normalized band-pass signal Bi (a similar situation could be graphed for the normalized high pass signal H). However, this time the two densities overlap because the region around zero now includes contributions from both, noise and structure. The solid line shows the noise reduction function $f^{NR}$ which is a "fuzzy" version of the clear-cut stepped unity-function in FIG. 6. As can be seen there is still a damping region around zero where the function $f^{NR}$ has a slope $\alpha_{min}$ less than one in a region around zero. For large signals y the function $f^{NR}$ has a slope $\alpha_{max} \geq 1$ which means a preservation or amplification of the signal. The function $f^{NR}$ has an inflection point $y_0$ and a slope control parameter $\gamma$ at said inflection point. In FIG. 7, $y_0=1.5$, with slope $\gamma=0.1$, it being understood these numbers are merely for representative or exemplary purposes and are in one embodiment user adjustable. Inflection point location will usually be of order unity ($y_0 \approx 1+/-2.0$). By varying the quantities $y_0$, $\gamma$ the user can "fine-tune" the location ($y_0$) at which the damping transitions into a preservation/amplification and how smoothly ($\gamma$) this transitions happens. The smooth transition of a damping action into an amplification (or at least preservation) action is to model the fact that in reality at locations around 0 to 1 one has both, structure and noise signals and the preponderance of the noise contribution tappers off the more the normalized band-pass $B_i/\sigma_i$ or high-pass $H/\sigma_i$ signals differs from zero (in particularly, normalized band-pass $B_i/\sigma_i$ or high-pass $H/\sigma_i$ signals larger than 1. Statistically, one has observed a tendency for the normalized image signal to be representative of structure (rather than noise) the more it differs from zero.

As a variant to all of the above embodiments for $f^{NR}$, the parameter $\alpha_{min}$ or $\alpha_{max}$ in Table 1 may not necessarily remain constant over their respective intervals, so the amount of amplification or damping may itself change in some configurations of $f^{NR}$. For instance, as mentioned above for configuration iii) in connection with FIG. 3, in one embodiment, all three actions of preserving, amplifying and damping are envisaged for the noise reduction function $f^{NR}$. For instance, in this "hybrid" embodiment, the function $f^{NR}$ may be configured, as before, as a damper for values inside an interval around zero and as a preserver for values outside this interval. Bu eventually, for very large values (say larger than some threshold value $y_1$) the function $f^{NR}$'s slope turns larger then unity so as to amplify (and not merely preserve) these larger values from $y_1$ onwards. The function $f^{NR}$ may be configured to transition from preserver to amplifier in a stepped manner (as in FIG. 6) or smoothly similar to the embodiment in in FIG. 7. For instance, in FIG. 7, rather than having $a_{max}=1$ for all values outside interval $|y|<<y_0$, $a_{max}$ may abruptly change into $a_{max}>1$ at $y_0$ or may smoothly transition into $a_{max}>1$ through an interval around $y_1$.

In another embodiment the noise reduction function can differ from point symmetry around zero. This allows to treat positive and negative contrasts differently. For instance to enhance "white spots" and preserve "black holes".

Referring back to step S530, after application of the noise reduction function to the normalized band or high pass images, the so (possibly modified) values are then re-weighted by multiplication of the standard deviation of the respective noise model for the band or high pass image under consideration. Application of $f^{NR}$ and reweighting is done for each level in i in the pyramid. The normalized, possibly modified and re-weighted frequency component images $H, L_i, B_i$ are then summed as per the recursion formula (1),(2) or (3) to reconstruct the noise reduced image $I^{NR}$.

Finally at step S540 the noise reduced image $I^{NR}$ is then outputted.

Referring now back to FIGS. 6,7 and in particular to the slope $a_{min}$ of the noise reduction function $f^{NR}$, it has been found that applicant at the said slope can be related to an dose increase recorded at the detector. More particularly, the slope can be related to a virtual dose increase. In yet other words the noise reduction effect that is achieved by the specific slope $\alpha_{min}$ is similar to a noise reduction effectively obtained by increasing the x-ray dose in acquiring the image.

In an ideal situation as illustrated in FIG. 6 said virtual dose increase has been found to be proportional to the reciprocal of the square of the slope. More particularly, the reciprocal of the squared slope is proportional to the reciprocal of the variance (that is the square for standard deviational of the noise at the respective pixel value) which in turn is proportional to the square of the local contrast noise ratio, that is the values of the high or band normalized images which in turn is proportional to the dose. In yet other words, whilst changing the slope parameter of the noise reduction function $f^{NR}$ (designated in the above forms as $\alpha_{min}$) one can simulate a noise reduction that could have been achieved had the image been acquired with a higher dose. The above observations on the physical meanings of the noise reduction variables can be put to good use by providing useful user interaction functionalities.

For instance, some or all of the noise reduction parameters $a_{min}$, $a_{max}$, $y_0$ and $\gamma$ are user adjustable. For instance in one embodiment a parameter nr may be defined that controls the strength of noise reduction which can adjusted by means of a suitable user interface. This parameter is mapped to the slope at the origin of the noise reduction function $f^{NR}$ as follows:

$$\alpha_{min} = (1-nr) \quad (13)$$

This is highly user intuitive, because now a large parameter nr means a larger damping and hence stronger noise reduction action.

Alternatively the noise reduction parameter can be replaced by a "virtual dose increase" parameter $vDose_{inc}$. Due to the considerations in connection with FIG. 6 above, this parameter is mapped to the slope of the noise reduction function $f^{NR}$ in the following way:

$$a_{min} = \frac{1}{\sqrt{vDose_{inc}}} \quad (14)$$

If for example the user wishes to simulate a doubling of the dose ($vDose_{enh}=2$), $\alpha_{min}$ is set to 0.71. In other words, the user can input a desired virtual dose increase $vDose_{enh}$ to so simulate a noise reduction that would have been achieved with a related dose increase. For instance, in one embodiment a graphical user interface is envisaged, having a window portion for display of the noise reduced version $I^{NR}$ of the original image I. A slider widget or similar graphical input means allows the user to adjust the virtual dose increase parameter in response of which $\alpha_{min}$ is recomputed as per (14) and so is the noise reduced version $I^{NR}$ based on the updated noise reduction function $f^{NR}$. In this manner the user can ascertain the benefits of a higher dosage X-ray image. The user can then decide to still acquire an (additional) x-ray image at this or other dose which then can be registered and added to the previously acquired image. This allows the user to initially apply low dose to the patient and successively acquire additional images on demand. This effectively decrease the dose applied to the patient. This allows a rational allocation of imaging equipment and patent dosage savings.

In other embodiment, it is also the structure amplification factor $\alpha_{max}$ that is user adjustable so the users can decide whether they wish structure signals to be merely preserved or even amplified.

As mentioned briefly above, inflection point location and slope may also be adjusted to define where and how quickly $f^{NR}$'s damping action is to transition into one of preservation or amplification.

As mentioned above in relation to FIGS. 3,4 the proposed noise reduction method can be combined with a contrast enhancement stage CE similar to the one described in DE 19 849 090. The multi scale decomposition representation (1) from above can be used for both, the noise reduction as proposed herein and the image contrast enhancement of DE 19 849 090. As described in DE 19 849 090, the contrast enhancement CE is based on contrast enhancement curves. These are applied after the noise reduction function for each band pass level and the high pass (multiplication with gain curves is omitted here for simplicity):

$$I^{C,NR} = f_H^C(f^{NR}(H/\sigma_H)\sigma_H) + \sum_{i=0}^{n-1} U^i f_i^C(f^{NR}(B_i/\sigma_i)\sigma_i) + U^n f^D(L_n) \quad (15)$$

The contrast enhancement curves are denoted by $f_i^C$ (i=H, 0, ..., n-1) and the global contrast enhancement curve ("film density curve") is denoted by $f^D$. The film density $f^D$ curve implements a density correction stage as in DE 19 849 090, page 5 line 6. The contrast enhancement curves $f_i^C$ implement a weak contrast curve as in DE 19 849 090, page 3 line 45 (FIG. 4). The combination of the proposed noise reduction method with this or other contrast enhancement algorithms is optional and only envisaged in some embodiments. That is, in other, alternative embodiments, there is no contrast enhancement stage.

Figure 8:
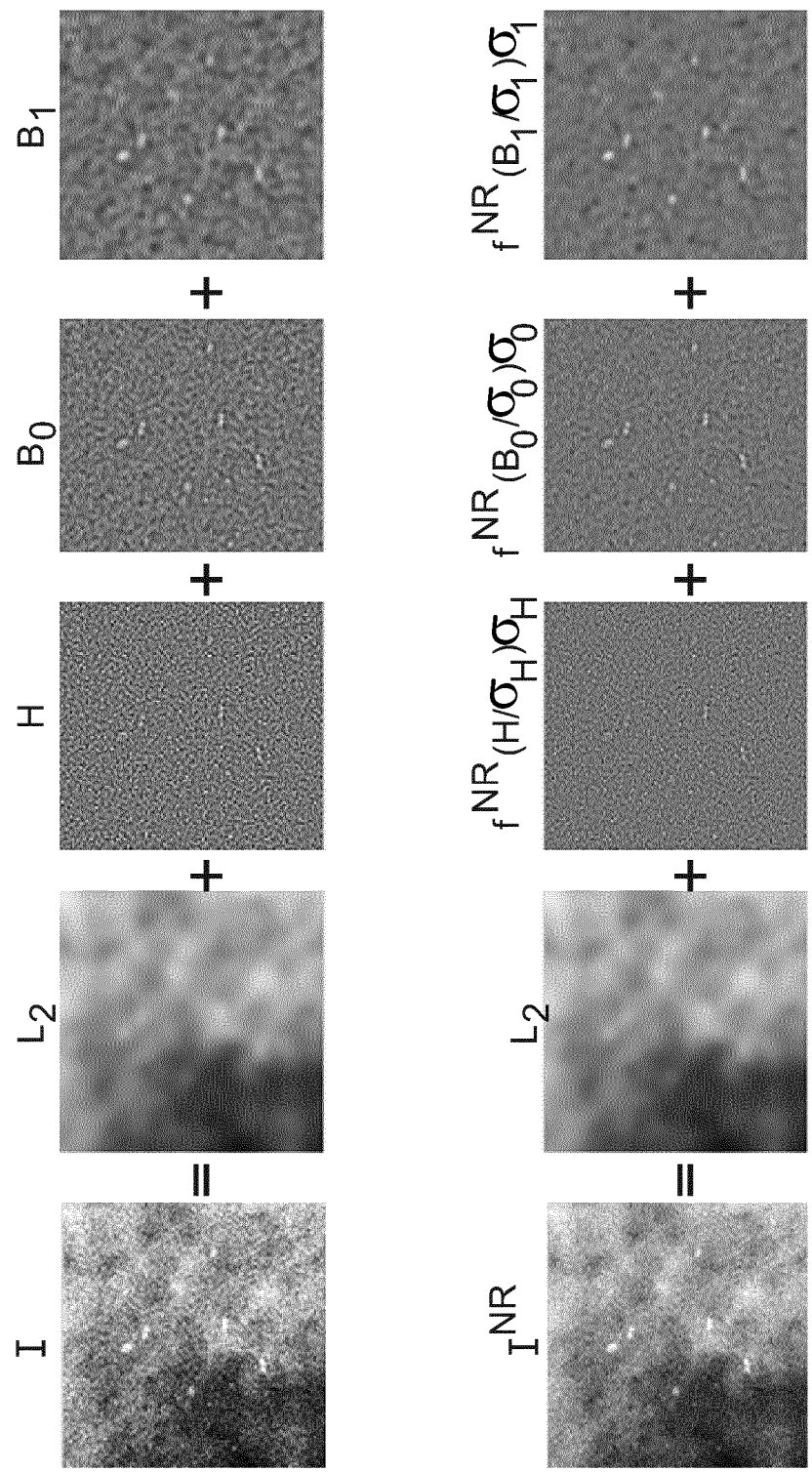
FIG. 8 shows a multi scale decomposition of an image into its spatial frequency component images and noise normalizations of said images.

Reference is now made to FIG. 8 where the upper row shows an example of a multi-scale decomposition of an image I into its components, low pass image L, high pass image H and two band pass images $B_0$ and $B_1$. It should be understood that the images in general have different sizes but are shown here scaled to equal size for illustrative purposes. The lower row shows the respective normalized high and band pass images with the applied noise reduction.

Figure 9:
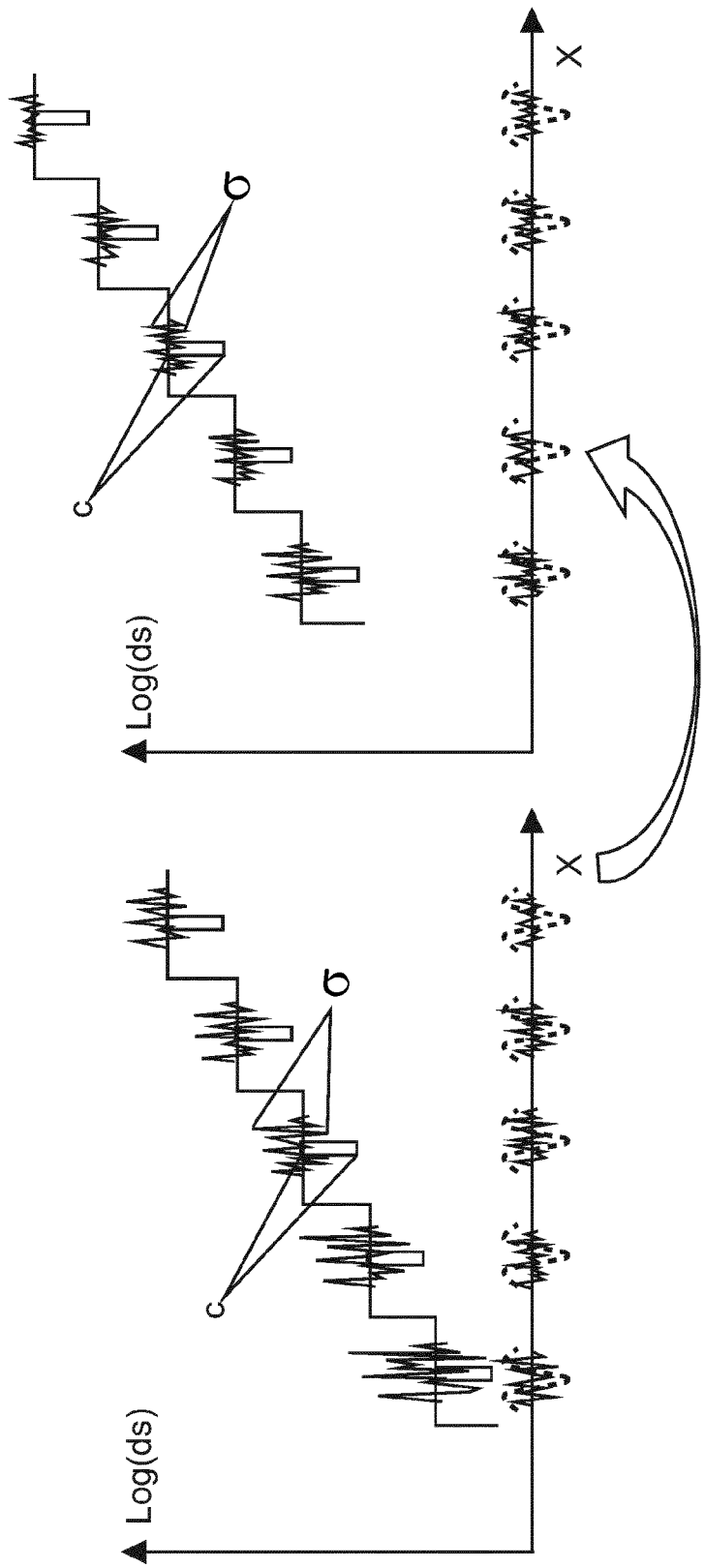
FIG. 9 shows an effect of a dose increase obtainable by the noise reduction method as proposed herein.

Referring now to FIG. 9 this illustrates the effect of dose increase which is simulated by the proposed noise reduction algorithm. The left hand side of the FIG. 9 shows in profile the various grey values of an x-ray image acquired at a certain dosage of a step-phantom. The right hand side shows a corresponding image acquired at a higher dosage. By adjusting the noise reduction parameters, in particularly the damping parameter $\alpha_{min}$, the user will be able to transform the noise amplitudes within the steps of the lower dosage image on the left hand side into those of the right hand side image by gradually increasing the damping factor $\alpha_{min}$ during the virtual dose increase simulation. Symbol $\sigma$ denotes the noise standard deviation within the steps of the phantom and c denotes a contrast element which should be preserved as far as possible.

Another use of the stepped or stair phantom (with or without the high contrast objects/inserts) to understand the effects of the proposed noise reduction method, is to acquire an image with a certain dose and the proposed noise reduction is then performed on the resulting x-ray image. Then each step of the phantom is associated with a specific received dose. Now the two images (that is, one image before and one image after noise reduction) are compared in the following way: The standard deviations of the noise before and after noise reduction are determined for each dose step. Then the ratio of the standard deviations before and after noise reduction is approximately equal to the inverse slope in the origin of the noise reduction function ($1/\alpha_{min}>1$). This holds true for each dose step and also for each frequency band pass if a decomposition according to equation (3) is performed before and after noise reduction. Furthermore the object contrasts within each dose step should not be significantly reduced by noise reduction as is indicated in FIG. 9.

The proposed method and apparatus NR can be applied to medical applications, where the visibility of structures or anomalies can be enhanced by noise reduction. Examples for such kind of structures or anomalies are micro-calcifications in mammography or lung nodules in radiologic thorax images. Furthermore the proposed method generally improves the image quality of diagnostic x-ray images by reducing noise while contrasts are mostly conserved. This is in particular desirable for fluoroscopic image sequences, where single images have typically a high amount of noise due to a low amount of applied dose per image.

The noise reduction module NR may be arranged as a software module or routine with suitable interfaces to pick up the detector DT signals and may be run on a general purpose computing unit or a dedicated computing unit. For instance they may be executed on a workstation or console CLS of the imager IMA. The noise reduction module NR with some or all of its components of may be resident on the executive agency (such as a general purpose computer, workstation or console) or may be accessed remotely/centrally by the executive agency via a suitable communication network in a distributed architecture.

The components of the noise reduction module NR may also be arranged as dedicated FPGAs or as hardwired standalone chips. However, this is an exemplary embodiment only. The components may be programmed in a suitable scientific computing platform such as Matlab® or Simulink® and then translated into C++ or C routines maintained in a library and linked when called on by the executive agency such as the general purpose computer, workstation or console.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above-described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

| | Definitions |
|---|---|
| B | Band pass |
| d | Decade factor for log dose domain |
| Dose Domain | The scale linear intensity values are transformed to by a monotonic function |
| e, q, f | Coefficients for electronic, quantum, fixed pattern noise, respectively |
| $f^D$ | Film density curve |
| $F_m$ | Binomial filter with kernel size m |
| $\downarrow, \uparrow$ | elementary down and up sampling operators |
| D, U | down and up sampling operators: $D = \downarrow F_m$, $U = F_m \uparrow$ |
| $f^{NR}$ | noise reduction function |
| $f_i^C$ | Band specific contrast enhancement function |
| H | High pass |
| I | Original image |
| L | Low pass |
| M | Dose domain mapping |
| $S^{lin}$ | Detector signal in the linear dose domain |
| $S^{log}$ | Detector signal in the logarithmic dose domain |
| σi | Band specific standard deviation for noise |

The invention claimed is:

1. An image processing method for processing image signals, comprising:
   receiving an X-ray image;
   decomposing the X-ray image into spatial frequency component images comprising at least a low pass component image and at least one further spatial frequency component image, the at least one further spatial frequency component image comprising a high pass image or a high pass image and one or more bandpass images;
   normalizing the at least one further spatial frequency component image by:

applying a noise model to the at least one low pass component image;

using the applied noise model to extract noise information for a particular pixel of the high pass image or the bandpass image, wherein the noise information is modelled in said noise model as a function of X-ray dose;

selectively modifying the at least one normalized spatial frequency component image based on a strength of the image signals;

combining the at least one low pass component image and the at least one normalized spatial frequency component image into a reconstructed version of the received image; and outputting the reconstructed version of the received image.

2. The image processing method of claim 1, wherein modifying comprises damping or amplifying.

3. The image processing method of claim 1, wherein selectively modifying is achieved by applying a noise reduction function to the image signals, the function being defined on a range of the image signals.

4. The image processing method of claim 3, wherein the function is monotonically increasing over the range of the image signals.

5. The image processing method of claim 3, wherein the function is continuously differentiable.

6. The image processing method of claim 1, wherein a strength of the image signal damping or amplifying is adjustable.

7. The image processing method of claim 1, wherein the noise model is different for each of the spatial frequency component images.

8. An image processing apparatus for processing image signals, comprising:

a signal input configured to receive an X-ray image;

a processor configured to:
  decompose the image into spatial frequency component images comprising at least a low pass component image and at least one further spatial frequency component image, the at least one further spatial frequency component image comprising a high pass image or a high pass image and one or more bandpass images;
  normalize the at least one further spatial frequency component image by:
    applying a noise model to the at least one low pass component image;
    using the applied noise model to extract noise information for a particular pixel of the high pass image or the bandpass image, wherein the noise information is modelled in the noise model as a function of X-ray dose;
  selectively modify the at least one normalized spatial frequency component image based on a strength of the image signals;
  combine the at least one low pass component image and the at least one normalized spatial frequency component image into a reconstructed version of the received image; and
a signal output configured to output the reconstructed version of the received image.

9. The image processing apparatus of claim 8, wherein selectively modifying comprises damping or amplifying.

10. The image processing apparatus of claim 8, wherein selectively modifying is achieved by applying a noise reduction function to the image signals, the function being defined on a range of the image signals.

11. A non-transitory computer-readable medium having one or more executable instructions stored thereon, which when executed by a processor, cause the processor to perform a method for processing image signals, the method comprising:

receiving an X-ray image;

decomposing the X-ray image into spatial frequency component images comprising at least a low pass component image and at least one further spatial frequency component image, the at least one further spatial frequency component image comprising a high pass image or a high pass image and one or more bandpass images;

normalizing the at least one further spatial frequency component image by:
  applying a noise model to the at least one low pass component image;
  using the applied noise model to extract noise information for a particular pixel of the high pass image or the bandpass image, wherein the noise information is modelled in said noise model as a function of X-ray dose;

selectively modifying the at least one normalized spatial frequency component image based on a strength of the image signals;

combining the at least one low pass component image and the at least one normalized spatial frequency component image into a reconstructed version of the received image; and outputting the reconstructed version of the received image.

* * * * *